United States Patent
Yamane

(10) Patent No.: US 11,839,431 B2
(45) Date of Patent: Dec. 12, 2023

(54) OPTICAL SYSTEM, FUNDUS EXAMINATION APPARATUS, FUNDUS IMAGING APPARATUS, AND FUNDUS EXAMINATION SYSTEM

(71) Applicant: TAMRON CO., LTD., Saitama (JP)

(72) Inventor: Kodai Yamane, Saitama (JP)

(73) Assignee: TAMRON CO., LTD., Saitama (JP)

(*) Notice: Subject to any disclaimer, the term of this patent is extended or adjusted under 35 U.S.C. 154(b) by 434 days.

(21) Appl. No.: 17/099,037

(22) Filed: Nov. 16, 2020

(65) Prior Publication Data
US 2021/0307607 A1  Oct. 7, 2021

(30) Foreign Application Priority Data
Apr. 7, 2020 (JP) ................. 2020-069116

(51) Int. Cl.
*A61B 3/12* (2006.01)
*A61B 3/14* (2006.01)
*A61B 3/00* (2006.01)
*G02B 27/28* (2006.01)

(52) U.S. Cl.
CPC .............. *A61B 3/12* (2013.01); *A61B 3/0008* (2013.01); *A61B 3/14* (2013.01); *A61B 3/1225* (2013.01); *G02B 27/286* (2013.01)

(58) Field of Classification Search
CPC ........... A61B 3/12; A61B 3/0008; A61B 3/14; A61B 3/1225; G02B 27/283; G02B 27/286; G02B 27/0018
USPC ........................................................ 351/215
See application file for complete search history.

(56) References Cited

U.S. PATENT DOCUMENTS

| | | | |
|---|---|---|---|
| 2,111,187 A * | 3/1938 | Keeler | A61B 3/1208 351/215 |
| 5,303,709 A * | 4/1994 | Dreher | A61B 3/1225 600/587 |
| 5,713,047 A | 1/1998 | Kohayakawa | |
| 2002/0012099 A1* | 1/2002 | Miwa | A61B 3/156 351/215 |
| 2004/0012853 A1* | 1/2004 | Garcia | G02B 21/0068 359/489.08 |

(Continued)

FOREIGN PATENT DOCUMENTS

| | | |
|---|---|---|
| JP | H05-337087 A | 12/1993 |
| JP | H09-028675 A | 2/1997 |
| JP | H09-028677 A | 2/1997 |

OTHER PUBLICATIONS

Lopez Morales "Spatially Resolved Polarimetry using Conventional and Unconventional Polarization States" PHD Thesis (Year: 2017).*

(Continued)

*Primary Examiner* — George G. King
(74) *Attorney, Agent, or Firm* — Paratus Law Group, PLLC

(57) ABSTRACT

An optical system for observing reflected light from a fundus includes: an irradiation unit for irradiating an eye with light exited from a light source; a light-acceptance unit for accepting reflected light reflected on a fundus of the eye; and a polarization control unit for making light irradiated to the eye z-polarization axisymmetric with respect to an optical axis and blocking the z-polarization of reflected light reflected on the eye and directed to the light-acceptance unit.

15 Claims, 4 Drawing Sheets

(56) References Cited

U.S. PATENT DOCUMENTS

| | | | | |
|---|---|---|---|---|
| 2007/0146632 A1* | 6/2007 | Chipman | ............... | G01J 4/04 |
| | | | | 351/205 |
| 2015/0002817 A1* | 1/2015 | Alasaarela | ............. | A61B 3/14 |
| | | | | 351/208 |
| 2021/0396509 A1* | 12/2021 | Bouma | ............ | G01N 21/4795 |

OTHER PUBLICATIONS

Sobczak et al. "In vivo measurements of corneal birefringence properties using the one-way reflective Mueller polarimetry" Optics Express vol. 29, No. 10, pp. 15356-15365 (Year: 2021).*

Nara Institute of Science and Technology, Miniaturized infrared cameras take colored photos of the eye, Retrieved from https://www.jst.go.jp/pr/announce/20180618/index.html, Jun. 18, 2018, pp. 1-7.

* cited by examiner

OPTICAL SYSTEM, FUNDUS EXAMINATION APPARATUS, FUNDUS IMAGING APPARATUS, AND FUNDUS EXAMINATION SYSTEM

CROSS-REFERENCE TO RELATED APPLICATIONS

This application is based on and claims the benefit of priority from Japanese Patent Application No. 2020-069116, filed on Apr. 7, 2020, the entire contents of which are incorporated herein by reference.

BACKGROUND OF THE INVENTION

Technical Field

The present invention relates to a fundus imaging apparatus.

Related Art

Three major causes of blindness in the Japanese are known: diabetic retinopathy, age-related macular degeneration, and glaucoma. Fundus examination is effective for early detection of these diseases. A fundus camera used in fundus examination uses an optical system of coaxial epi-illumination in which the optical axis of light incident on the eye and the optical axis of reflected light reflected by the fundus coincide with each other. Therefore, there is a problem that unnecessary light reflected not on the fundus but on the surface of the eye is mixed with the light forming the fundus image, and ghost flare occurs.

As a technique for solving such a problem, there are known techniques described in JP 9-28677 A, JP 5-337087 A, and JP 9-28675 A, and Nara Institute of Science and Technology, Japan Science and Technology Agency, "Miniaturized infrared cameras take colored photos of the eye", [Online], Jun. 18, 2018, jointly announced by JST, [Searched on Jan. 14, 2020], Internet (URL:https://www.jst.go.jp/pr/announce/20180618/index.html). JP 9-28677 A and JP 5-337087 A describe a method of preventing overlapping of optical paths between irradiation light and reflected light by separating the irradiation light. JP 9-28675 A discloses a method of imaging and shielding unnecessary light. Nara Institute of Science and Technology, Japan Science and Technology Agency, "Miniaturized infrared cameras take colored photos of the eye" describes a method of blocking unnecessary light by using a linear polarization device.

However, the above-described conventional techniques have the following problems. With the methods described in JP 9-28677 A and JP 5-337087 A, when the irradiation light has a wide angle, most of the optical paths of the irradiation light and the reflected light overlap, and it is not possible to prevent occurrence of ghost flare. With the method described in JP 9-28675 A, when the irradiation light has a wide angle, the image becomes large, and hence necessary light is also blocked. With the method described in Nara Institute of Science and Technology, Japan Science and Technology Agency, "Miniaturized infrared cameras take colored photos of the eye", reflected light from a space other than a space parallel or orthogonal to the optical axis of the polarization device, for example, has an angle different from that of the polarization direction, and hence rotation occurs in the polarization direction, and unnecessary light cannot be fully blocked by the linear polarization device.

Therefore, for example, even when the irradiation light has a wide angle, there is a demand for a fundus examination apparatus having an optical system that appropriately blocks unnecessary light and suppresses occurrence of ghost flare.

It is an object of an aspect of the present invention to realize an optical system capable of appropriately blocking unnecessary light and suppressing occurrence of ghost flare, and various apparatuses using the optical system.

SUMMARY OF THE INVENTION

In order to solve the above problems, the optical system according to an aspect of the present invention is an optical system for observing reflected light from the fundus, the optical system including: an irradiation unit for irradiating the eye with light exited from a light source; a light-acceptance unit for accepting reflected light reflected on the fundus of the eye; and a polarization control unit for making light irradiated to the eye z-polarization axisymmetric with respect to an optical axis and blocking the z-polarization of reflected light reflected on the eye and directed to the light-acceptance unit.

The fundus imaging apparatus according to an aspect of the present invention includes the optical system, and the light-acceptance unit is a camera for imaging reflected light from the fundus.

The fundus examination apparatus according to an aspect of the present invention includes the optical system, and the light-acceptance unit is a lens for observing reflected light from the fundus.

The fundus examination system according to an aspect of the present invention includes the fundus examination apparatus.

According to an aspect of the present invention, it is possible to realize an optical system capable of appropriately blocking unnecessary light and suppressing occurrence of ghost flare, and various apparatuses using the optical system.

DESCRIPTION OF THE EMBODIMENTS

Hereinafter, an embodiment of the present invention will be described in detail.

First Embodiment

Figure 1:
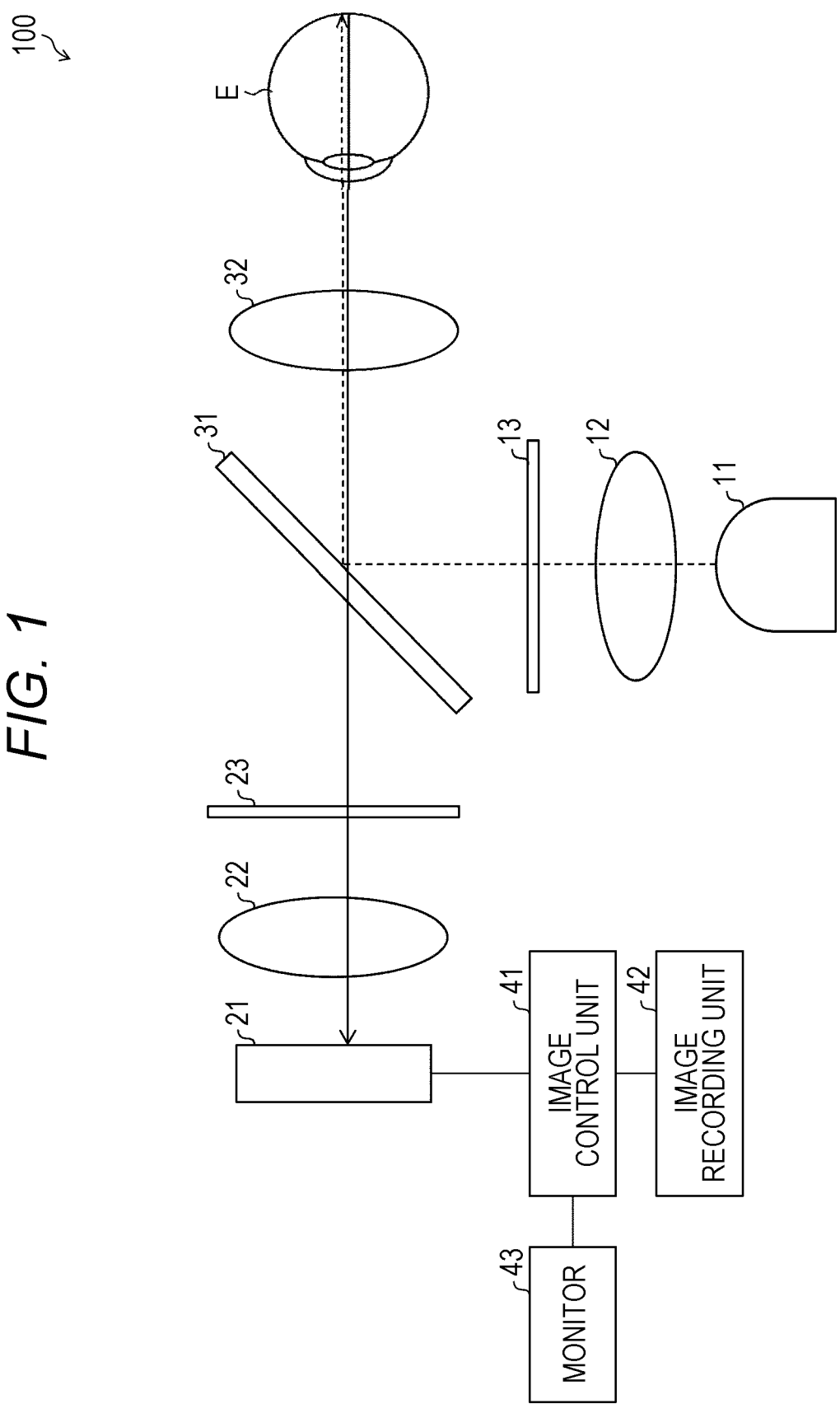
FIG. 1 is a view schematically showing an example of an optical system according to a first embodiment of the present invention.

FIG. 1 is a view schematically showing an example of an optical system 100 according to the first embodiment of the present invention. As shown in FIG. 1, the optical system 100 is an optical system for observing reflected light from a fundus of an eye E. The optical system 100 is an optical system of coaxial epi-illumination. The optical system 100 includes an irradiation unit, a light-acceptance unit, and a polarization control unit. The optical system 100 is an optical system of coaxial epi-illumination in which the optical axis of light irradiated to the eye E and the optical axis of reflected light from the eye E coincide with each other.

Configuration Example

As shown in FIG. 1, the optical system 100 includes a light source 11, a lens 12, a first z-polarizer 13, a beam splitter 31, a lens 32, a second z-polarizer 23, a lens 22, and a camera 21. The camera 21 can transmit/receive data to/from an image control unit 41. The image control unit 41 is connected to an image recording unit 42 and a monitor 43. In FIG. 1, an optical path of exit light exited from the light source 11 and irradiated to the eye E is indicated by a broken line, and an optical path of reflected light reflected on the eye E and directed to the camera 21 is indicated by a solid line.

The irradiation unit is to irradiate the eye E with light exited from the light source 11. The light-acceptance unit is to accept reflected light reflected on the fundus of the eye E. In the present embodiment, the light-acceptance unit is the camera 21. Thus, the fundus imaging apparatus can be realized by using the camera 21 as the light-acceptance unit of the optical system 100.

The polarization control unit is to make light irradiated to the eye E z-polarization axisymmetric with respect to an optical axis and to block the z-polarization of reflected light reflected on the eye E and directed to the light-acceptance unit. In the present embodiment, the polarization control unit is two z-polarizers, i.e., the first z-polarizer 13 and the second z-polarizer 23.

In the optical system 100, the beam splitter 31 is disposed on the optical axis of the light source 11, and the camera 21 is disposed on the axis orthogonal to the optical axis of the beam splitter 31. The eye E of the subject to be observed is disposed at a position facing the camera 21. On the light source 11 side relative to the beam splitter 31, the lens 12 and the first z-polarizer 13 are disposed in this order from the light source 11 side. The lens 32 is disposed between the beam splitter 31 and the eye E. On the camera 21 side relative to the beam splitter 31, the second z-polarizer 23 and the lens 22 are disposed in this order from the beam splitter 31 side.

The light source 11 may be a stroboscopic light source or a continuous light source such as a heat bulb, an LD, or an LED. The light source 11 may be a near infrared irradiation apparatus that emits light having a wavelength equal to or greater than 600 nm and equal to or less than 1700 nm. It is preferable because the subject hardly feels glare due to the light source 11 that irradiates near infrared rays having a wavelength equal to or greater than 600 nm and equal to or less than 1700 nm. The near infrared irradiation apparatus is a near infrared LED, for example. The near infrared LED is advantageous from the viewpoint of reduction in size and weight. Other than that, the near infrared irradiation apparatus may include a halogen lamp and a Fabry-Perot bandpass filter that transmits near infrared rays of a specific wavelength, or may be a heat radiation ceramic heater to which a metasurface structure that efficiently extracts heat radiation light is applied.

The camera 21 is, for example, a color sensor or monochrome sensor of a solid-state image sensor such as CCD, CMOS, or InGaAs. The camera 21 converts an image imaged by light reflected by the retina present in the fundus of the eye E of the subject into image data. In the present description, imaging of the fundus means forming of an image by focusing the light reflected by the fundus on the image sensor.

The conversion of the image data in the camera 21 is controlled by the image control unit 41. The image control unit 41 is connected to an image recording unit 42 and a monitor 43. The image data converted in the camera 21 is recorded in the image recording unit 42 or displayed on the monitor 43 by the image control unit 41. The image recording unit 42 writes/reads image data into/from a nonvolatile recording medium such as an HDD, an SSD, or a DVD-RAM.

The beam splitter 31 reflects the exit light exited from the light source 11 in a direction orthogonal to its optical axis, and transmits the reflected light reflected by the eye E and directed to the camera 21. That is, the beam splitter 31 splits the optical path of the exit light exited from the light source 11 and the optical path of the reflected light reflected by the eye E and directed to the camera 21.

The lenses 12, 22, and 32 are disposed such that the pencil of light of the exit light exited from the light source 11 or the reflected light reflected by the eye E and directed to the camera 21 is appropriately spread or narrowed down.

The z-polarizer is a polarizer that transmits, of the incident light, the z-polarization axisymmetric with respect to the optical axis. The z-polarization axisymmetric with respect to the optical axis is radial polarization in which the electric field vector is distributed in the radial direction, or azimuth polarization in which the electric field vector is distributed in the azimuth direction. The polarization directions of the radial polarization and the azimuth polarization are orthogonal to each other. In the present description, a polarizer that transmits radial polarization is referred to as a radial polarizer, and a polarizer that transmits azimuth polarization is referred to as an azimuth polarizer.

The first z-polarizer 13, which is one of the two z-polarizers included in the polarization control unit, is disposed in the optical path of only the exit light exited from the light source 11. That is, the first z-polarizer 13 is disposed in the optical path from the light source 11 to the beam splitter 31. In the optical system 100, the first z-polarizer 13 is disposed between the lens 12 and the beam splitter 31. The first z-polarizer 13 may be disposed between the light source 11 and the lens 12.

The second z-polarizer 23, which is the other of the two z-polarizers included in the polarization control unit, is disposed in the optical path of only the light directed to the camera 21. That is, the second z-polarizer 23 is disposed in the optical path from the beam splitter 31 to the camera 21. In the optical system 100, the second z-polarizer 23 is disposed between the beam splitter 31 and the lens 22. The second z-polarizer 23 may be disposed between the lens 22 and the camera 21.

The first z-polarizer 13 is a polarizer that transmits first z-polarization, which is z-polarization of exit light exited from the light source 11. The second z-polarizer 23 is a polarizer that transmits second z-polarization, which is orthogonal to the first z-polarization. That is, the second z-polarizer 23 transmits the second z-polarization of the light reflected by the eye E and directed to the camera 21. The polarization directions of the first z-polarization and the second z-polarization are orthogonal to each other. Therefore, the second z-polarization is azimuth polarization when the first z-polarization is radial polarization, and the second z-polarization is radial polarization when the first z-polarization is azimuth polarization.

Operation Example

Here, the movement of light in the optical system 100 will be described with an example of a case where the first z-polarizer 13 is a radial polarizer and the second z-polarizer 23 is an azimuth polarizer. The exit light exited from the light source 11 passes through the lens 12 to spread the pencil of light, and the radial polarization transmits the first z-polarizer 13. The radial polarization having transmitted through the first z-polarizer 13 is reflected by the beam splitter 31 in the direction of the eye E, and passes through the lens 32 to narrow down the pencil of light, and is incident on the eye E.

The reflected light incident on and reflected by the eye E passes through the lens 32 to spread the pencil of light, transmits the beam splitter 31, and is incident on the second z-polarizer 23. As for the reflected light, at the second z-polarizer 23, the azimuth polarization is transmitted and the radial polarization is blocked. The azimuth polarization having transmitted through the second z-polarizer 23 passes through the lens 22 to narrow down the pencil of light, is accepted and imaged by the camera 21, and is converted into image data. Thus, in the optical system 100, image data of the fundus is obtained on the basis of the reflected light from the fundus.

The light incident on the eye E reaches the fundus and is reflected on the fundus, reaches the fundus and diffuses backward, or does not reach the fundus and is reflected on the surface of the eye. That is, the reflected light reflected by the eye E includes not only the return light from the fundus necessary for imaging a fundus image, but also unnecessary light that is reflected on the surface of the eye and causes ghost flare.

The radial polarization incident on the eye E and having reached the fundus is reflected by the fundus, and loses the polarization state. On the other hand, the radial polarization reflected on the surface of the eye E without reaching the fundus is maintained in a polarization state. Therefore, the return light from the fundus included in the reflected light is not radial polarization, and the unnecessary light is radial polarization. When the reflected light is incident on the second z-polarizer 23, the unnecessary light that is radial polarization does not transmit and is blocked, and the return light from the fundus that is not radial polarization transmits as the azimuth polarization. As a result, the reflected light accepted by the camera 21 does not include unnecessary light, and ghost flare is not generated.

Thus, the optical system 100 has the first z-polarizer 13 and the second z-polarizer 23 as a polarization control unit that makes light irradiated to the eye E z-polarization axisymmetric with respect to the optical axis and blocks the z-polarization of reflected light reflected on the eye E and directed to the light-acceptance unit. This makes it possible to appropriately block unnecessary light included in the reflected light reflected by the eye E, and suppress occurrence of ghost flare.

It is preferable that the first z-polarization, which is the z-polarization of the exit light exited from the light source 11, is the radial polarization. That is, it is preferable that the first z-polarizer 13 is a radial polarizer and the second z-polarizer 23 is an azimuth polarizer. This is because the radial polarization, which is P-polarized light, has less reflection on the surface of the eye E and has higher light utilization efficiency.

A light-blocking mask having a doughnut-shaped opening and a condenser lens may be disposed between the light source 11 and the lens 12. In this case, it is further preferable that the light-blocking mask surface, as the light source position, has a conjugate relationship with the vicinity of the fundus of the eye E. It is preferable that the size of the image in the vicinity of the fundus of the eye E is within 2 mm, more preferably within 1 mm. Thus, it is possible to prevent variation in the rotation of the polarization due to variation in the incident direction with respect to the eye E.

(First Modification)

At least one of the first z-polarizer 13 and the second z-polarizer 23, which are two z-polarizers that make the light irradiated to the eye E z-polarization axisymmetric with respect to the optical axis, may be configured to have a linear polarizer that transmits the linear polarization of the incident light, and a half wave plate unit that converts the linear polarization having transmitted through the linear polarizer into polarization axisymmetric with respect to the optical axis. Thus, the z-polarizer may be configured by combining a linear polarizer and a half wave plate unit. Such a half wave plate unit can be realized by forming, into one plate shape, a plurality of half wave plates having different axial orientations by predetermined angles along a direction extending radially or concentrically from a center overlapping the optical axis when viewed in plan.

For example, the z-polarizer is constituted of a linear polarizer and a half wave plate unit in which a plurality of half wave plates obtained by forming, into one plate shape, a plurality of half wave plates having different axial orientations by predetermined angles along a direction extending radially from a center overlapping the optical axis when viewed in plan.

For example, the half wave plate unit has a half wave plate corresponding to four regions of the first to fourth regions divided into regions divided by two orthogonal straight lines passing through the center of the planar shape. The half wave plate of the first region is a half wave plate in which the vibration direction of the passing light passes through the center and is inclined by 45° with respect to the reference line, for example. The half wave plate of the second region is a half wave plate in which the vibration direction of the passing light passes through the center and is inclined by 135° with respect to the reference line. The half wave plate of the third region is a half wave plate in which the vibration direction of the passing light passes through the center and is inclined by 225° with respect to the reference line. The half wave plate of the fourth region is a half wave plate in which the vibration direction of the passing light passes through the center and is inclined by 315° with respect to the reference line.

The half wave plate unit emits linear polarization inclined by 45° from the reference line from the first region, emits linear polarization inclined by 135° from the reference line from the second region, emits linear polarization inclined by 225° from the reference line from the third region, and emits linear polarization inclined by 315° from the reference line from the fourth region. Thus, the z-polarizer emits linear polarization that is inclined by 90° with respect to exit light of the adjacent region, and this exit light exhibits substantially the same action as that of the radial polarization in the first embodiment.

Similarly, a z-polarizer that substantially emits azimuth polarization can be formed when the half wave plate of the first region is disposed in the second region with the same orientation, the half wave plate of the second region is disposed in the third region with the same orientation, the half wave plate of the third region is disposed in the fourth region with the same orientation, and the half wave plate of the fourth region is disposed in the first region with the same orientation. In the embodiment of the present invention, such a z-polarizer may be used.

(Second Modification)

Furthermore, at least one of the first z-polarizer 13 and the second z-polarizer 23, which are two z-polarizers that make the light irradiated to the eye E z-polarization axisymmetric with respect to the optical axis, may have a light-blocking section that blocks light at its optical center. The light-blocking section is formed, for example, by blackening a portion of the z-polarizer corresponding to the vicinity of the center of incident light, or by providing a reflection film to the portion. Examples of such a reflection film include a metal film and a dielectric film. When the z-polarizer is a wire grid polarizer, a light-blocking section may be formed by not providing a groove of the wire grid at its optical center.

In the z-polarizer, a portion corresponding to the vicinity of the center of incident light has a lower axisymmetric polarization characteristic than that in another portion. In such an optical system, direct reflection is most avoided. Therefore, deterioration of the characteristics of the z-polarizer can be prevented by providing in advance a configuration in which a portion having such low characteristics or a portion where direct reflection may occur does not transmit light.

(Third Modification)

Furthermore, at least one of the first z-polarizer 13 and the second z-polarizer 23, which are two z-polarizers that make the light irradiated to the eye E z-polarization axisymmetric with respect to the optical axis, may have, at its optical center, a linear polarizer section that allows linear polarization to pass through. Of the light irradiated to the eye E and the reflected light from the eye E, the light on and in the vicinity of the optical axis is light substantially parallel to the optical axis. Therefore, there is substantially no disadvantage that unnecessary light having an orientation of a relatively large angle with respect to the optical axis transmits the linear polarizer. In addition, combination of linear polarizers having polarization directions orthogonal to each other allows the light-acceptance unit to sufficiently accept the light in the vicinity of the optical axis of the reflected light of the fundus.

Here, the range of the center as the linear polarizer section can be appropriately set within a range where no trouble occurs due to light having an angle with respect to the optical axis. The size of the center may be calculated by computer simulation, or a range free from the above trouble may be experimentally specified by an experiment using a linear polarizer instead of a z-polarizer.

Therefore, at least one of the first z-polarizer 13 and the second z-polarizer 23 may be a radial polarizer and have, at its optical center, a linear polarizer section that allows longitudinal linear polarization to pass through. At least one of the first z-polarizer 13 and the second z-polarizer 23 may be an azimuth polarizer and have, at its optical center, a linear polarizer section that allows lateral linear polarization to pass through. Even with the polarizer having such a configuration, the incident light can be z-polarization axisymmetric with respect to the optical axis.

Second Embodiment

Other embodiments of the present invention will be described below. For convenience of explanation, members having the same functions as those described in the above embodiment are denoted by the same reference numerals, and description thereof will not be repeated.

Figure 2:
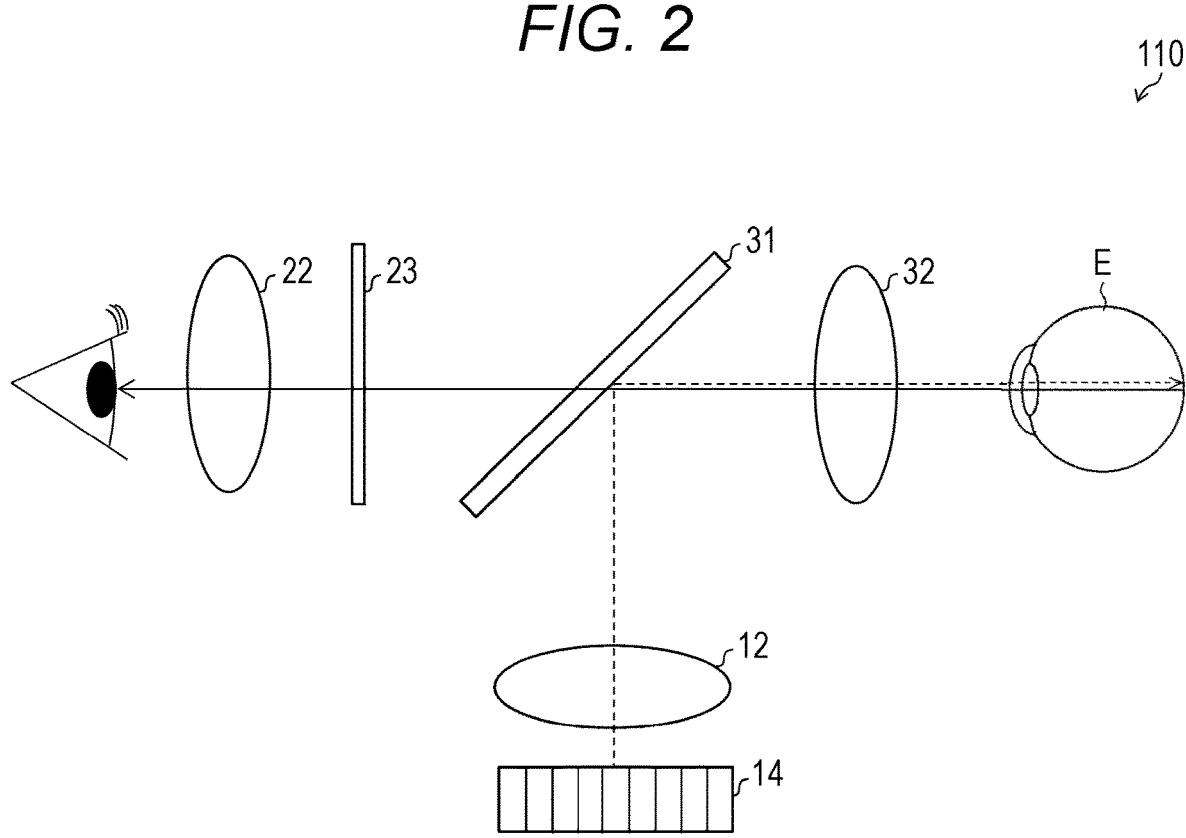
FIG. 2 is a view schematically showing an example of an optical system according to a second embodiment of the present invention.

FIG. 2 is a view schematically showing an example of an optical system 110 according to a second embodiment of the present invention. The optical system 110 is an optical system of coaxial epi-illumination. As shown in FIG. 2, the optical system 110 is different from the optical system 100 of the first embodiment shown in FIG. 1 in that the optical system has a light source 14 and the second z-polarizer 23 as a polarization control unit. Therefore, in the present embodiment, only the points different from the first embodiment will be described in detail, and other details will be omitted.

Configuration Example

As shown in FIG. 2, the optical system 110 includes the light source 14, the lens 12, the beam splitter 31, the lens 32, the second z-polarizer 23, and the lens 22. In the present embodiment, the light-acceptance unit is the lens 22. In the optical system 110, the lens 22 is an eyepiece, and an image is formed by focusing the light reflected by the fundus of the eye E, and hence the observer observes and examines the fundus image through the eyepiece. Thus, the fundus examination apparatus can be realized by using the lens 22 as the light-acceptance unit of the optical system 110.

In the optical system 110, the polarization control unit, by using the light source 14 and the second z-polarizer 23, makes light irradiated to the eye E z-polarization axisymmetric with respect to an optical axis and blocks the z-polarization of reflected light reflected on the eye E and directed to the light-acceptance unit. That is, the optical system 110 uses, instead of the first z-polarizer 13 in the optical system 100 according to the first embodiment, the light source 14 that emits the first z-polarization.

In the optical system 110, the beam splitter 31 is disposed on the optical axis of the light source 14, and an eye that observes a fundus image through the lens 22 is positioned on the axis of the beam splitter 31 orthogonal to the optical axis. The eye E of the subject to be observed is disposed at a position facing the lens 22. The lens 12 is disposed on the light source 14 side relative to the beam splitter 31. The lens 32 is disposed between the beam splitter 31 and the eye E. The second z-polarizer 23 is disposed between the beam splitter 31 and the lens 22.

The light source 14 emits first z-polarization, which is z-polarization. As the light source 14, for example, it is possible to use a light source configured to emit z-polarization by arraying laser light sources, a light source configured to emit light in a z-polarization state, a light source configured to emit z-polarization by maximizing the angular dependence of light with a mirror, and the like.

Operation Example

Here, the movement of light in the optical system 110 will be described with an example of a case where the light source 14 is a light source that emits radial polarization and the second z-polarizer 23 is an azimuth polarizer. The radial polarization exited from the light source 14 passes through the lens 12 to spread the pencil of light, and is reflected in the direction of the eye E by the beam splitter 31. The radial polarization reflected on the beam splitter 31 passes through the lens 32 to narrow down the pencil of light, and is incident on the eye E.

The reflected light incident on and reflected by the eye E passes through the lens 32 to spread the pencil of light, transmits the beam splitter 31, and is incident on the second z-polarizer 23. As for the reflected light, at the second z-polarizer 23, the azimuth polarization is transmitted and the radial polarization is blocked. The azimuth polarization transmitted through the second z-polarizer 23 is imaged at the lens 22, and the imaged image is observed and examined by the observer through the lens 22.

The radial polarization having exited from the light source 14 and reached the fundus is reflected by the fundus, and loses the polarization state. On the other hand, the radial polarization reflected on the surface of the eye E without reaching the fundus is maintained in a polarization state. Therefore, the return light from the fundus included in the reflected light is not radial polarization, and the unnecessary light is radial polarization. When the reflected light is incident on the second z-polarizer 23, the unnecessary light that is radial polarization does not transmit and is blocked, and the return light from the fundus that is not radial polarization transmits as the azimuth polarization. As a result, the reflected light accepted by the lens 22 does not include unnecessary light, and ghost flare is not generated.

Thus, the optical system 110 has the light source 14 and the second z-polarizer 23 as a polarization control unit that makes light irradiated to the eye E z-polarization axisymmetric with respect to the optical axis and blocks the z-polarization of reflected light reflected on the eye E and directed to the light-acceptance unit. This makes it possible to appropriately block unnecessary light included in the reflected light reflected by the eye E, and suppress occurrence of ghost flare.

Third Embodiment

Other embodiments of the present invention will be described below. For convenience of explanation, members having the same functions as those described in the above embodiment are denoted by the same reference numerals, and description thereof will not be repeated.

Figure 3:
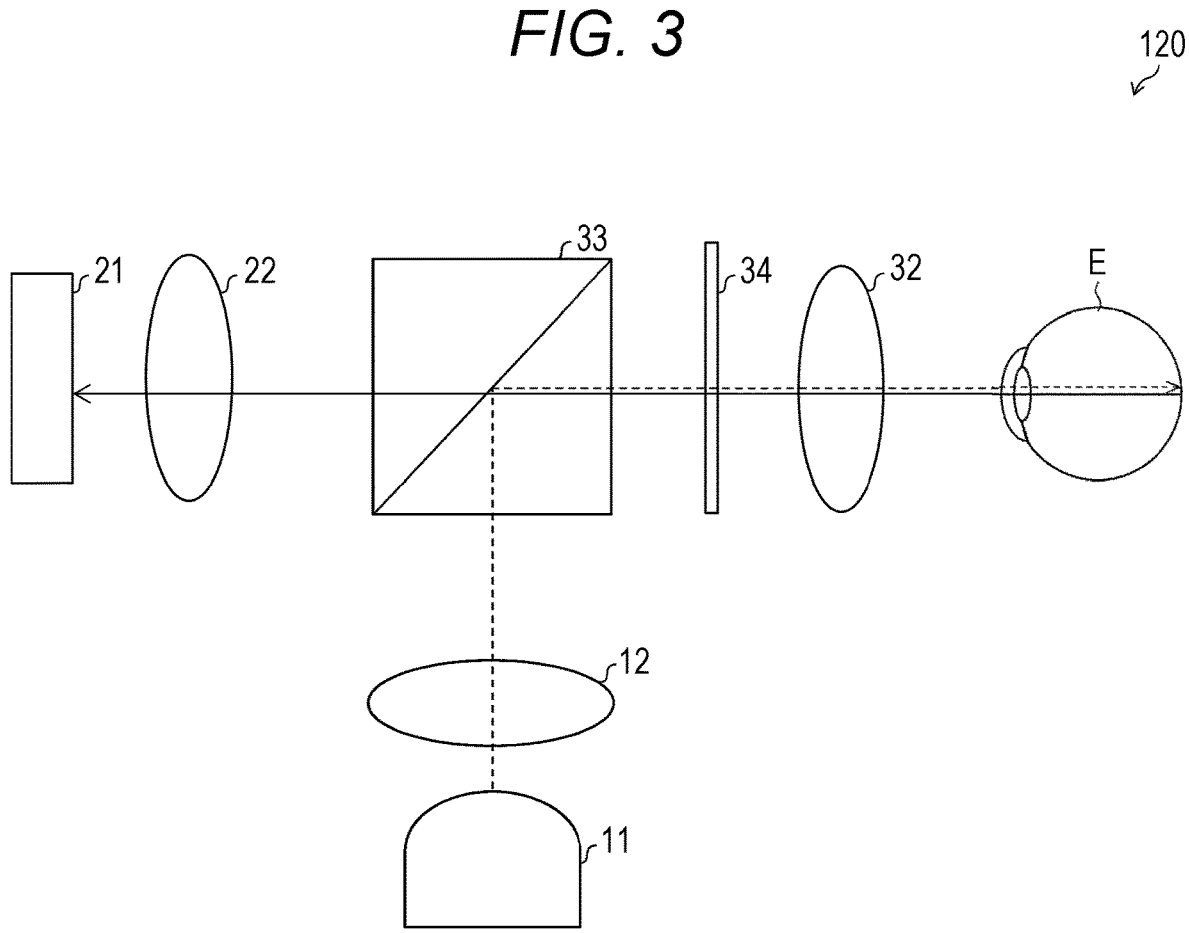
FIG. 3 is a view schematically showing an example of an optical system according to a third embodiment of the present invention.

FIG. 3 is a view schematically showing an example of an optical system 120 according to a third embodiment of the present invention. The optical system 120 is an optical system of coaxial epi-illumination. As shown in FIG. 3, the optical system 120 is different from the optical system 100 of the first embodiment shown in FIG. 1 in that the optical system has a polarization beam splitter 33 as a polarization control unit. Therefore, in the present embodiment, only the points different from the first embodiment will be described in detail, and other details will be omitted.

Configuration Example

As shown in FIG. 3, the optical system 120 includes the light source 11, the lens 12, the polarization beam splitter 33, a polarization correction device 34, the lens 32, the lens 22, and the camera 21. In the optical system 120, the polarization control unit, by using the polarization beam splitter 33, makes light irradiated to the eye E z-polarization axisymmetric with respect to an optical axis and blocks the z-polarization of reflected light reflected on the eye E and directed to the light-acceptance unit. That is, the optical system 120 uses, instead of the first z-polarizer 13 and the second z-polarizer 23 in the optical system 100 according to the first embodiment, the polarization beam splitter 33. The polarization beam splitter 33 reflects, of incident light, linear polarization of an arbitrary angle, and transmits linear polarization orthogonal to the linear polarization of the arbitrary angle.

In the optical system 120, the polarization beam splitter 33 is disposed on the optical axis of the light source 11, and the camera 21 is disposed on the axis orthogonal to the optical axis of the polarization beam splitter 33. The eye E of the subject to be observed is disposed at a position facing the camera 21. The lens 12 is disposed on the light source 11 side relative to the polarization beam splitter 33. Between the polarization beam splitter 33 and the eye E, the polarization correction device 34 and the lens 32 are disposed in this order from the polarization beam splitter 33 side. The lens 22 is disposed between the polarization beam splitter 33 and the camera 21.

The polarization beam splitter 33 has a dielectric film tilted at a predetermined angle in a transparent body, for example. The polarization beam splitter 33 reflects, of incident light, a linear polarization component of an arbitrary angle of incident light, and transmits a linear polarization component of an angle orthogonal to the arbitrary angle. Therefore, the polarization beam splitter 33 reflects, of incident light, for example, a component of radial polarization, and transmits the polarization in an orientation orthogonal to the radial polarization. In this case, the light transmitting the polarization beam splitter 33 is substantially a component of azimuth polarization of the incident light. Alternatively, the polarization beam splitter 33 reflects, of incident light, for example, a component of azimuth polarization, and transmits the polarization in an orientation orthogonal to the azimuth polarization. In this case, the light transmitting the polarization beam splitter 33 is substantially a component of azimuth polarization of the incident light. Thus, the polarization beam splitter 33 makes one z-polarization of the radial polarization and the azimuth polarization incident on the eye E. That is, the polarization beam splitter 33 makes one of the first z-polarization and the second z-polarization, which is z-polarization of the incident light, incident on the eye E, and transmits the other light.

The polarization correction device 34 corrects the orientation of the z-polarization reflected by the polarization beam splitter 33. The polarization correction device 34 may be provided in one or both of the optical path between the polarization beam splitter 33 and the eye E and the optical path between the polarization beam splitter 33 and the camera 21. In the case where polarization as reflected light of the polarization beam splitter 33 is used, a component in the rotation direction is sometimes included in the polarization direction due to the reflection. The polarization correction device 34 eliminates the influence of the component in the rotation direction in the polarization generated by such the reflection of the polarization. The polarization correction device 34 corrects, for example, the orientation of polarization including a component in the rotation direction by reflection, and returns the orientation to the orientation before polarization. As the polarization correction device 34, it is possible to use a wave plate corresponding to the change in the orientation occurring in the light reflected by the polarization beam splitter 33. Alternatively, the polarization correction device 34 may block only the component in the rotation direction having been generated.

Operation Example

Here, the movement of light in the optical system 120 will be described with an example of a case where the polarization beam splitter 33 reflects radial polarization and transmits light other than polarization. The light exited from the light source 11 passes through the lens 12 to spread the pencil of light, and is incident on the polarization beam splitter 33. In the polarization beam splitter 33, of the incident light, radial polarization is directed to the eye E, and light other than the radial polarization is transmitted. The radial polarization directed from the polarization beam splitter 33 to the eye E passes through the polarization correction device 34 to correct its orientation, passes through the lens 32 to narrow down the pencil of light, and is incident on the eye E.

The reflected light incident on and reflected by the eye E passes through the lens 32 to spread the pencil of light, passes through the polarization correction device 34, and is incident on the polarization beam splitter 33. The polarization beam splitter 33 reflects, of the incident light, the radial polarization, and transmits light other than the radial polarization. That is, the polarization beam splitter 33 blocks radial polarization and transmits light other than the radial polarization. Light other than the radial polarization having transmitted through the polarization beam splitter 33 passes through the lens 22 to narrow down the pencil of light, is accepted and imaged by the camera 21, and is converted into image data.

The radial polarization having been directed from the polarization beam splitter 33 to the eye E and reached the fundus is reflected by the fundus, and loses the polarization state. On the other hand, the radial polarization reflected on the surface of the eye E without reaching the fundus is maintained in a polarization state. Therefore, the return light from the fundus included in the reflected light is not radial polarization, and the unnecessary light is radial polarization. When this reflected light is incident on the polarization beam splitter 33, the unnecessary light that is radial polarization is not transmitted and is blocked, and the return light from the fundus that is not the radial polarization is transmitted. As a result, the reflected light accepted by the camera 21 does not include unnecessary light, and ghost flare is not generated.

Thus, the optical system 120 has the polarization beam splitter 33 as a polarization control unit that makes light irradiated to the eye E z-polarization axisymmetric with respect to the optical axis and blocks the z-polarization of reflected light reflected on the eye E and directed to the light-acceptance unit. This makes it possible to appropriately block unnecessary light included in the reflected light reflected by the eye E, and suppress occurrence of ghost flare.

Fourth Embodiment

Other embodiments of the present invention will be described below. For convenience of explanation, members having the same functions as those described in the above embodiment are denoted by the same reference numerals, and description thereof will not be repeated.

Figure 4:
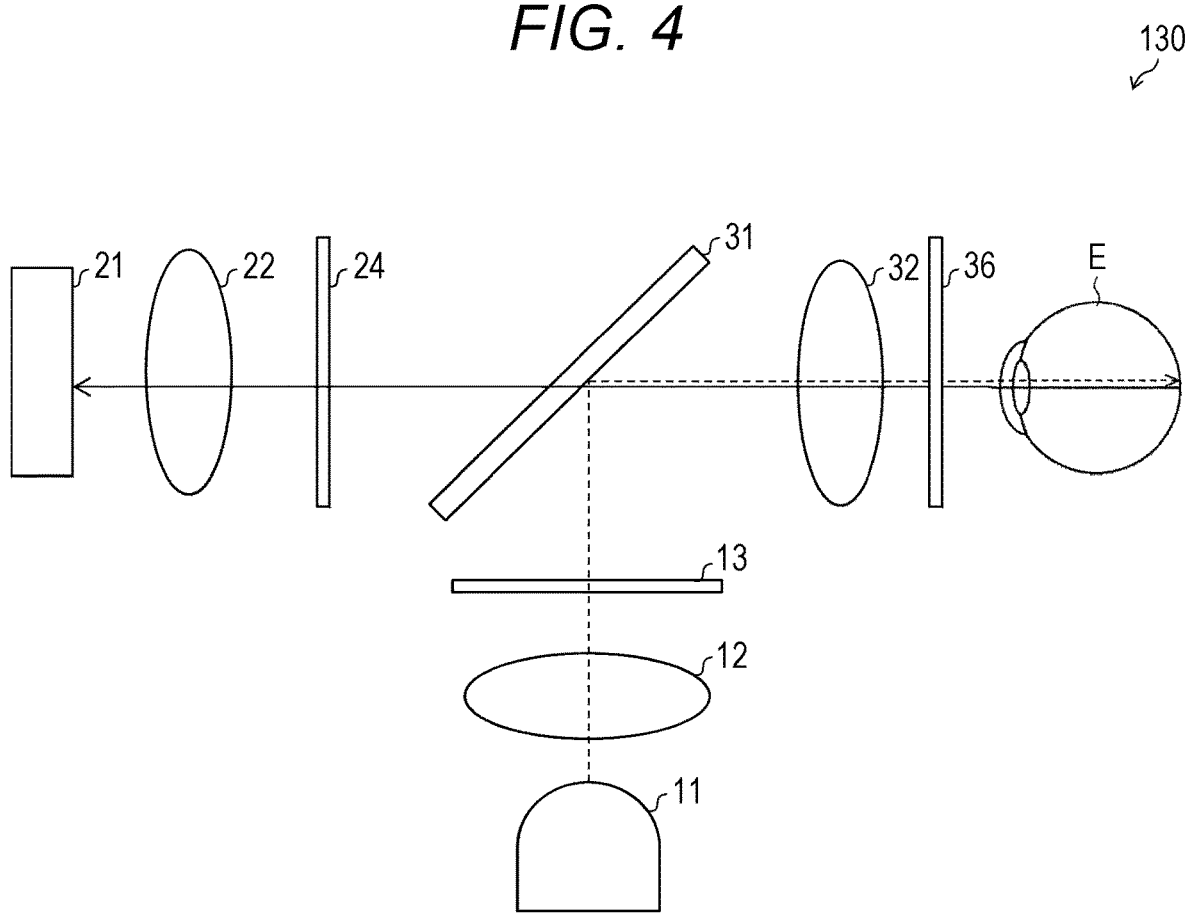
FIG. 4 is a view schematically showing an example of an optical system according to a fourth embodiment of the present invention.

FIG. 4 is a view schematically showing an example of an optical system 130 according to a fourth embodiment of the present invention. The optical system 130 is an optical system of coaxial epi-illumination. As shown in FIG. 4, the optical system 130 is different from the optical system 100 of the first embodiment shown in FIG. 1 in that the optical system has the first z-polarizer 13 and a first z-polarizer 24, which are two first z-polarizers, and a quarter wave plate (polarization rotation unit) 36 as a polarization control unit. Therefore, in the present embodiment, only the points different from the first embodiment will be described in detail, and other details will be omitted.

Configuration Example

As shown in FIG. 4, the optical system 130 includes the light source 11, the lens 12, the first z-polarizer 13, the beam splitter 31, the lens 32, the quarter wave plate 36, the first z-polarizer 24, the lens 22, and the camera 21.

In the optical system 130, the two first z-polarizers and the quarter wave plate 36 make light irradiated to the eye E z-polarization axisymmetric with respect to the optical axis and block the z-polarization of reflected light reflected on the eye E and directed to the light-acceptance unit. That is, the optical system 130 has, instead of the first z-polarizer 13 and the second z-polarizer 23 in the optical system 100 according to the first embodiment, the first z-polarizer 13 and the first z-polarizer 24, which are the two first z-polarizers, and the quarter wave plate 36 as a polarization control unit.

In the optical system 130, the beam splitter 31 is disposed on the optical axis of the light source 11, and the camera 21 is disposed on the axis orthogonal to the optical axis of the beam splitter 31. The eye E of the subject to be observed is disposed at a position facing the camera 21. On the light source 11 side relative to the beam splitter 31, the lens 12 and the first z-polarizer 13 are disposed in this order from the light source 11 side. Between the beam splitter 31 and the eye E, the lens 32 and the quarter wave plate 36 are disposed in this order from the beam splitter 31 side. Between the beam splitter 31 and the camera 21, the first z-polarizer 24 and the lens 22 are disposed in this order from the beam splitter 31 side.

The first z-polarizer 13 is one of the polarizers that is disposed in the optical path of only the exit light exited from the light source 11 and transmits the z-polarization of the exit light. The first polarizer 24 is the other of the z-polarizers that is disposed in the optical path of only the light directed to the camera 21 and transmits the z-polarization of the reflected light. That is, the first z-polarizer 13 and the first z-polarizer 24 are different only in the optical path to be disposed and have the identical function. Therefore, in the case where the first z-polarizer 13 is a radial polarizer, the first z-polarizer 24 is also a radial polarizer, and in the case where the first z-polarizer 13 is an azimuth polarizer, the first z-polarizer 24 is also an azimuth polarizer.

The quarter wave plate 36 is disposed in the optical paths of both the light irradiated to the eye E and the reflected light from the eye E. That is, both light incident on the eye E and light reflected from the eye E are incident on the quarter wave plate 36. The quarter wave plate 36 gives a phase difference of λ/4 to the incident light, and is provided by arraying or distributing the slow axes in accordance with the polarization direction of the incident light.

Operation Example

Here, the movement of light in the optical system 130 will be described with an example of a case where the first z-polarizer 13 and the first z-polarizer 24 are radial polarizers. The pencil of light exited from the light source 11 is spread through the lens 12, and the radial polarization transmits the first z-polarizer 13. The radial polarization having transmitted through the first z-polarizer 13 is reflected in the direction of the eye E by the beam splitter 31, passes through the lens 32 to narrow down the pencil of light, and is incident on the quarter wave plate 36. The radial polarization incident on the quarter wave plate 36 becomes circular polarization and is incident on the eye E.

The illumination light of circular polarization incident on the eye E and having reached the fundus is reflected by the fundus, and loses the polarization state. On the other hand, the illumination light of circular polarization reflected on the surface of the eye E without reaching the fundus is maintained in a polarization state. The light reflected by the eye is incident on the quarter wave plate 36 again. The light incident on the quarter wave plate 36 becomes circular polarization in a predetermined direction (Here, for the purpose of explanation, the circular polarization in this predetermined direction is assumed to be clockwise circular polarization with the direction in which the camera faces being positive. The same is true hereinafter unless otherwise specified). Therefore, the illumination light of circular polarization reflected on the surface of the eye E is further rotated in phase and becomes azimuth polarization. That is, the unnecessary light reflected on the surface of the eye E passes through the quarter wave plate 36 and hence becomes azimuth polarization.

Thus, the quarter wave plate 36 rotates the phase of the light incident thereon, and emits, to the light-acceptance unit (camera 21) side, the z-polarization of azimuth angle rotated by 90° with respect to the azimuth angle of the z-polarization incident on the quarter wave plate 36 from the light source side. That is, the quarter wave plate 36 functions as a polarization rotation unit that rotates the phase of incident light. On the other hand, since the light having reached and been reflected on the fundus has lost the polarization state, the polarization state varies even if the light passes through the quarter wave plate 36, and not all of the light becomes azimuth polarization. In the present embodiment, the polarization rotation unit rotates the azimuth angle of incident light by 90°, but the rotation angle of light exited to the light-acceptance unit side is not limited to this.

The reflected light having passed through the quarter wave plate 36 passes through the lens 32 to spread the pencil of light, passes through the beam splitter, and is incident on the first z-polarizer 24. Of the reflected light, the return light having reached and been reflected on the fundus transmits the first z-polarizer 24, but the unnecessary light having become azimuth polarization does not transmit the first z-polarizer 24 and is blocked. The return light having passed through the first z-polarizer 24 passes through the lens 22 to narrow down the pencil of light, is accepted and imaged by the camera 21, and is converted into image data. That is, the unnecessary light reflected on the surface of the eye is blocked by the first z-polarizer 24 and does not reach the camera 21, and only the return light from the fundus is accepted by the camera 21.

Thus, the optical system 130 has the first z-polarizer 13 and the first z-polarizer 24, which are the two first z-polarizers, and the quarter wave plate 36 as a polarization control unit that makes light irradiated to the eye E z-polarization axisymmetric with respect to the optical axis and blocks the z-polarization of reflected light reflected on the eye E and directed to the light-acceptance unit. This makes it possible to appropriately block unnecessary light included in the reflected light reflected by the eye E, and suppress occurrence of ghost flare.

Modification of Fourth Embodiment

Instead of the quarter wave plate 36, a 45° azimuthal polarizer may be used as the polarization rotation unit. In the case of using the 45° azimuthal polarizer, similarly to the case of using the quarter wave plate 36, the two first z-polarizers and the 45° azimuthal polarizer make light irradiated to the eye E z-polarization axisymmetric with respect to the optical axis and block the z-polarization of reflected light reflected on the eye E and directed to the light-acceptance unit. That is, the optical system of the modification of the fourth embodiment has the two first z-polarizers and the 45° azimuthal polarizer as a polarization control unit. The 45° azimuthal polarizer rotates its azimuth angle by 45° without changing the polarization state of the incident light.

Here, the movement of light in the optical system of the modification of the fourth embodiment having the 45° azimuthal polarizer will be described with an example of a case where both of the two first z-polarizers are radial polarizers. In this case, the radial polarization having transmitted through the first z-polarizer 13 is incident on the 45° azimuthal polarizer. The radial polarization incident on the 45° azimuthal polarizer becomes the radial polarization rotated by 45° and is incident on the eye E.

The radial polarization rotated by 45° incident on the eye E and having reached the fundus is reflected by the fundus, and loses the polarization state. On the other hand, the radial polarization rotated by 45° reflected on the surface of the eye E without reaching the fundus is maintained in a polarization state. The light reflected by the eye is incident on the 45° azimuthal polarizer again. Since the light incident on the 45° azimuthal polarizer becomes the light rotated by 45°, the radial polarization rotated by 45° having been reflected on the surface of the eye E is further rotated by 45° to become azimuth polarization. That is, the unnecessary light reflected on the surface of the eye E passes through the 45° azimuthal polarizer and hence becomes azimuth polarization. On the other hand, since the light having reached and been reflected on the fundus has lost the polarization state, the light only rotates by 45° even if the light passes through the 45° azimuthal polarizer, and the light does not become azimuth polarization.

Thus, the 45° azimuthal polarizer rotates the azimuth angle of the polarizer incident thereon, and emits, to the light-acceptance unit side, the z-polarization of azimuth angle rotated by 90° with respect to the azimuth angle of the z-polarization incident on the 45° azimuthal polarizer from the light source side. That is, the 45° azimuthal polarizer functions as a polarization rotation unit that rotates the phase of incident light. In the present modification, the polarization rotation unit rotates the azimuth angle of incident light by 90°, but the rotation angle of light exited to the light-acceptance unit side is not limited to this.

The reflected light having passed through the 45° azimuthal polarizer is incident on the first z-polarizer 24. Of the reflected light, the return light having reached and been reflected on the fundus transmits the first z-polarizer 24, but the unnecessary light having become azimuth polarization does not transmit the first z-polarizer 24 and is blocked.

Thus, according to the optical system of the modification example of the fourth embodiment, it is possible to appropriately block unnecessary light included in the reflected light reflected by the eye E, and suppress occurrence of ghost flare.

[Use of Optical System]

The optical system according to any of the first to fourth embodiments described above can be used in various apparatuses that obtain a fundus image by observing the reflected light of the fundus.

A fundus imaging apparatus including the optical system according to any of the first to fourth embodiments described above, wherein the light-acceptance unit is a camera for imaging a reflected light of the fundus, is included in the scope of the present invention. A fundus examination apparatus including the optical system according to any of the first to fourth embodiments described above, wherein the light-acceptance unit is a lens for observing a reflected light of the fundus, is also included in the scope of the present invention. A fundus examination system in which such a fundus examination apparatus is combined with a diagnostic apparatus, a surgical apparatus, or the like for eye diseases is also included in the scope of the present invention.

For example, a system that examines the fundus using an image imaged by a camera as a light-acceptance unit is only required to have a functional configuration that determines the image of the fundus having been imaged. Such an examination system may have a communication apparatus that inputs/outputs information including data of the image, if necessary.

The determination of an image of the fundus in the system can be performed by the following image determination model, for example.

[Regarding Image Determination Model]

As the image determination model, it is possible to use a model that outputs information regarding appropriateness of image data in response to input of information regarding a specific part of the image data. The image determination model may come in one type or more.

It is possible to cause the image determination model to perform learning by referring to the training data. The training data includes image data of the fundus of the subject and at least one piece of information regarding a part in an image corresponding to the image data.

The learning of the image determination model can be performed as follows, for example. That is, a sufficient number of image data of the fundus are prepared, and the state (e.g., size) of a specific part (e.g., optic disc and venous vessel) in the image is measured. A sufficient number of data by the measurement are acquired, the neural network is caused to learn the data, and the weight of the path is determined for each image data. Thus, the image determination model is created.

The image determination model and the method for causing the image determination model to perform learning can be appropriately selected within the range where the desired result is obtained. Examples of image determination models include neural networks and support vector machines. Examples of neural networks include convolutional neural networks (CNN), recurrent neural networks (RNN), and fully coupled neural networks. Examples of algorithms for causing the image determination model to perform learning include back propagation and ID3.

The image determination model may be other than a model based on machine learning. For example, the image determination model may be a regression model using the image data as an objective variable and using information regarding the appropriateness of the image data as an explanatory variable.

The fundus examination system according to the present embodiment can be performed in parallel with another examination for the eye such as a visual acuity test. Imaging of the fundus can also be performed by the subject himself/herself by a guidance function such as a voice guide. In this case, since an operator for imaging the fundus and image diagnosis of the fundus is not required, it is expected that the cost for fundus examination can be greatly reduced. According to the present embodiment, since fundus imaging is expected to be widespread, prevention of eye diseases is further promoted, and as a result, reduction in the number of patients who lose their eyesight due to eye diseases is expected.

Such a system can be implemented by a control unit including a random access memory (RAM) that develops a program for executing the system. The program may be supplied to a computer at another place via any transmission medium (communication networks, broadcast waves, or the like) capable of transmitting the program. The system described above can also be implemented in the form of a data signal embedded in a carrier wave, in which the program is embodied by electronic transmission. Alternatively, the control unit may be implemented by a logic circuit (hardware) formed in an integrated circuit (IC chip) or the like.

SUMMARY

An optical system according to a first aspect of the present invention is an optical system for observing reflected light from the fundus, the optical system including: an irradiation unit for irradiating the eye with light exited from a light source; a light-acceptance unit for accepting reflected light reflected on the fundus of the eye; and a polarization control unit for making light irradiated to the eye z-polarization axisymmetric with respect to an optical axis and blocking the z-polarization of reflected light reflected on the eye and directed to the light-acceptance unit. This makes it possible to appropriately block unnecessary light and suppress occurrence of ghost flare, and thus enables preferable observation of reflected light of the fundus.

In the optical system according to the second aspect of the present invention, the polarization control unit may have two z-polarizers, one of which may be a first z-polarizer that is disposed in an optical path of only exit light exited from the light source and transmits a first z-polarization, which is the z-polarization of the exit light, and the other of which may be a second z-polarizer that is disposed in an optical path of only light directed to the light-acceptance unit and transmits a second z-polarization, which is orthogonal to the first z-polarization. This makes it possible to provide another form of the polarization control unit.

In the optical system according to the third aspect of the present invention, the light source may emit a first z-polarization, which is the z-polarization, and the polarization control unit may have the light source, and a z-polarizer that is disposed in an optical path of only light directed to the light-acceptance unit and transmits second z-polarization orthogonal to the first z-polarization. This makes it possible to appropriately block unnecessary light and suppress occurrence of ghost flare, and thus enables preferable observation of reflected light of the fundus. This makes it possible to provide another form of the polarization control unit.

In the optical system according to the fourth aspect of the present invention, one of the first z-polarization and the second z-polarization may be radial polarization and the other may be azimuth polarization. This makes it possible to provide another form of the polarization control unit.

In the optical system according to the fifth aspect of the present invention, the first z-polarization may be radial polarization. This makes it possible to appropriately block unnecessary light and suppress occurrence of ghost flare, and thus enables preferable observation of reflected light of the fundus. It is possible to realize an optical system excellent in light utilization efficiency.

In the optical system according to the sixth aspect of the present invention, the polarization control unit may have one z-polarizer, which is disposed in an optical path of only exit light exited from the light source and transmits the z-polarization of the exit light, a polarization rotation unit, which is disposed in optical paths of both light irradiated to the eye and the reflected light from the eye and rotates a phase of incident light, and the other z-polarizer, which is disposed in an optical path of only light directed to the light-acceptance unit and transmits the z-polarization of the reflected light. This makes it possible to provide another form of the polarization control unit.

In the optical system according to the seventh aspect of the present invention, the z-polarizer may have a linear polarizer that transmits linear polarization of incident light, and a half wave plate unit that converts linear polarization having transmitted through the linear polarizer into polarization axisymmetric with respect to the optical axis, wherein in the half wave plate unit, a plurality of half wave plates having different axial orientations by predetermined angles along a direction extending radially or concentrically from a center overlapping the optical axis when viewed in plan may be formed into one plate shape. This makes it possible to provide another aspect of a z-polarizer that transmits polarization.

In the optical system according to the eighth aspect of the present invention, at least one of the polarizers may have a light-blocking section that blocks light at its optical center. Therefore, deterioration of the characteristics of the z-polarizer can be prevented by providing in advance a configuration in which a portion of the z-polarizer having such low characteristics or a portion of the z-polarizer where direct reflection may occur does not transmit light.

In the optical system according to the ninth aspect of the present invention, the z-polarizer may have, at its optical center, a linear polarizer section that allows linear polarization to pass through. This makes it possible to provide another form of the z-polarizer.

In the optical system according to the tenth aspect of the present invention, the polarization control unit may have a polarization beam splitter that reflects linear polarization of an arbitrary angle of incident light, and transmits linear polarization of an angle orthogonal to the arbitrary angle. This makes it possible to provide another form of the polarization control unit.

The optical system according to the eleventh aspect of the present invention may further have a polarization correction device that corrects an orientation of polarization reflected by the polarization beam splitter in one or both of an optical path between the polarization beam splitter and the eye and an optical path between the polarization beam splitter and the light-acceptance unit. This makes it possible to correct change in orientation of light reflected by the polarization beam splitter 33.

In the optical system according to the twelfth aspect of the present invention, the light source may be a near infrared irradiation apparatus that emits light having a wavelength equal to or greater than 600 nm and equal to or less than 1700 nm. It is preferable because the subject hardly feels glare due to this.

The fundus imaging apparatus according to the thirteenth aspect of the present invention includes the optical system according to any of the first to twelfth aspects, wherein the light-acceptance unit is a camera for imaging reflected light of the fundus. This makes it possible to realize a fundus imaging apparatus capable of appropriately blocking unnecessary light and suppressing occurrence of ghost flare, and thus enabling preferable observation of reflected light of the fundus.

The fundus examination apparatus according to the fourteenth aspect of the present invention includes the optical system according to any of the first to twelfth aspects, wherein the light-acceptance unit is a lens for observing reflected light of the fundus. This makes it possible to realize a fundus examination apparatus capable of appropriately blocking unnecessary light and suppressing occurrence of ghost flare, and thus enabling preferable observation of reflected light of the fundus.

The fundus examination system according to the fifteenth aspect of the present invention includes the fundus examination apparatus according to the fourteenth aspect. This makes it possible to realize a fundus examination system capable of appropriately blocking unnecessary light and suppressing occurrence of ghost flare, and thus enabling preferable observation of reflected light of the fundus.

The present invention is not limited to the embodiments described above, and various changes are possible within the scope of the claims, and embodiments obtained by appropriately combining technical means disclosed in different embodiments are also included in the technical scope of the present invention.

What is claimed is:

1. An optical system for observing reflected light from a fundus comprising:
   an irradiation unit for irradiating an eye with light exited from a light source;
   a light acceptor for accepting reflected light reflected on a fundus of the eye; and
   a polarization controller for making light irradiated to the eye z-polarization axisymmetric with respect to an optical axis and blocking the z-polarization of reflected light reflected on the eye and directed to the light acceptor.

2. The optical system according to claim 1, wherein
   the polarization controller has two z-polarizers,
   one of which is a first z-polarizer that is disposed in an optical path of only exit light exited from the light source and transmits a first z-polarization, which is the z-polarization of the exit light, and
   another of which is a second z-polarizer that is disposed in an optical path of only light directed to the light acceptor and transmits a second z-polarization, which is orthogonal to the first z-polarization.

3. The optical system according to claim 1, wherein
   the light source and the polarization controller emit a first z-polarization, which is the z-polarization, and
   the polarization controller has
   a z-polarizer that is disposed in an optical path of only light directed to the light acceptor and transmits a second z-polarization orthogonal to the first z-polarization.

4. The optical system according to claim 2, wherein one of the first z-polarization and the second z-polarization is radial polarization and another is azimuth polarization.

5. The optical system according to claim 4, wherein the first z-polarization is radial polarization.

6. The optical system according to claim 1, wherein
   the polarization controller has
   one z-polarizer, which is disposed in an optical path of only exit light exited from the light source and transmits the z-polarization of the exit light, a polarization rotation unit, which is disposed in optical paths of both light irradiated to the eye and the reflected light from the eye and rotates a phase of incident light, and another z-polarizer, which is disposed in an optical path of only light directed to the light acceptor and transmits the z-polarization of the reflected light.

7. The optical system according to claim 2, wherein at least one of the first z-polarizer and the second z-polarizer has
a linear polarizer that transmits linear polarization of incident light, and
a half wave plate unit that converts linear polarization having transmitted through the linear polarizer into polarization axisymmetric with respect to the optical axis, wherein
in the half wave plate unit,
a plurality of half wave plates having different axial orientations by predetermined angles along a direction extending radially or concentrically from a center overlapping the optical axis when viewed in plan is formed into one plate shape.

8. The optical system according to claim 2, wherein at least one of the z-polarizers has a light-blocking section that blocks light at its optical center.

9. The optical system according to claim 2, wherein at least one of the first z-polarizer and the second z-polarizer has, at its optical center, a linear polarizer section that allows linear polarization to pass through.

10. The optical system according to claim 1, wherein the polarization controller has
a polarization beam splitter that reflects linear polarization of an arbitrary angle of incident light, and transmits linear polarization of an angle orthogonal to the arbitrary angle.

11. The optical system according to claim 10 further comprising a wave plate that corrects an orientation of polarization reflected by the polarization beam splitter in one or both of an optical path between the polarization beam splitter and the eye and an optical path between the polarization beam splitter and the light acceptor.

12. The optical system according to claim 1, wherein the light source is a near infrared irradiation apparatus that emits light having a wavelength equal to or greater than 600 nm and equal to or less than 1700 nm.

13. A fundus imaging apparatus comprising the optical system according to claim 1, wherein the light acceptor is a camera for imaging reflected light of the fundus.

14. A fundus examination apparatus comprising the optical system according to claim 1, wherein the light acceptor is a lens for observing reflected light of the fundus.

15. A fundus examination system comprising:
the fundus examination apparatus according to claim 14;
an image control unit;
an image recording unit; and
a monitor.

* * * * *